US008568328B2

(12) United States Patent
Fujii et al.

(10) Patent No.: US 8,568,328 B2
(45) Date of Patent: Oct. 29, 2013

(54) ELECTRONIC BLOOD PRESSURE GAUGE FOR MEASURING BLOOD PRESSURE BY USING VOLUME COMPENSATION METHOD

(75) Inventors: Kenji Fujii, Kyoto (JP); Yukiya Sawanoi, Kyoto (JP); Naomi Matsumura, Kyoto (JP); Reiji Fujita, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 329 days.

(21) Appl. No.: 12/921,792

(22) PCT Filed: Mar. 13, 2009

(86) PCT No.: PCT/JP2009/054858
§ 371 (c)(1),
(2), (4) Date: Sep. 10, 2010

(87) PCT Pub. No.: WO2009/116461
PCT Pub. Date: Sep. 24, 2009

(65) Prior Publication Data
US 2011/0015531 A1 Jan. 20, 2011

(30) Foreign Application Priority Data

Mar. 19, 2008 (JP) ................................. 2008-071930

(51) Int. Cl.
*A61B 5/02* (2006.01)
(52) U.S. Cl.
USPC ............ 600/493; 600/481; 600/485; 600/490
(58) Field of Classification Search
USPC ................................................ 600/480–495
See application file for complete search history.

(56) References Cited

U.S. PATENT DOCUMENTS 5,241,963 A * 9/1993 Shankar ........................ 600/481
5,379,774 A 1/1995 Nishimura et al.
(Continued)

FOREIGN PATENT DOCUMENTS

JP 59-5296 A 1/1984
JP 6-165764 A 6/1994
(Continued)

OTHER PUBLICATIONS

Yamakoshi, K., et al., "Indirect Measurement of Instantaneous Arterial Blood Pressure in the Human Finger by the Vascular Unloading Technique," Biomedical Engineering, IEEE Transactions on , vol. BME-27, No. 3, pp. 150-155, Mar. 1980 (Yamakoshi, 1980).*

(Continued)

*Primary Examiner* — Michael Kahelin
*Assistant Examiner* — Mitchell Alter
(74) *Attorney, Agent, or Firm* — Osha Liang LLP

(57) ABSTRACT

An electronic sphygmomanometer, which measures blood pressure in accordance with the volume compensation method, detects a cuff pressure inside a cuff attached to a measurement site of the blood pressure. An arterial volume detection circuit detects an arterial volume signal of the measurement site. A drive control unit, after setting the cuff pressure to an initial cuff pressure, servo-controls a cuff pressure adjustment unit so that a volume of an artery becomes constant, based on the detected arterial volume signal. While the servo control is being performed, an arterial volume change amount is detected based on the detected arterial volume signal. In the servo control, when it is detected that the change amount in the arterial volume is minimal, a volume change elimination rate calculating unit calculates a volume change elimination rate (an amplitude of the arterial volume signal during the control/an amplitude of the arterial volume signal before the control) to output the same as a barometer of arteriosclerosis.

9 Claims, 13 Drawing Sheets

(56) References Cited

U.S. PATENT DOCUMENTS

2004/0220481 A1* 11/2004 Yokozeki et al. ............ 600/485
2009/0312652 A1* 12/2009 Yamakoshi et al. .......... 600/493

FOREIGN PATENT DOCUMENTS

| | | |
|---|---|---|
| JP | 9-122091 A | 5/1997 |
| JP | 2000-316821 A | 11/2000 |
| JP | 2004-195204 A | 7/2004 |
| JP | 2008-36004 A | 2/2008 |

OTHER PUBLICATIONS

International Search Report w/translation from PCT/JP2009/054858 dated Apr. 14, 2009 (2 pages).

Yamakoshi, K. et al.; "Indirect measurement of instantaneous arterial blood pressure in the rat"; American Physiological Society; 1979; pp. H632-H637 (6 pages).

Patent Abstracts of Japan; Publication No. 2008-036004 dated Feb. 21, 2008 (1 page).

Patent Abstracts of Japan; Publication No. 06-165764 dated Jun. 14, 1994 (1 page).

Patent Abstracts of Japan; Publication No. 2002-316821 dated Oct. 31, 2002 (1 page).

Patent Abstracts of Japan; Publication No. 09-122091 dated May 13, 1997 (1 page).

Patent Abstracts of Japan; Publication No. 2004-195204 dated Jul. 15, 2004 (1 page).

Patent Abstracts of Japan; Publication No. 59-000529 dated Jan. 5, 1984 (1 page).

* cited by examiner

ELECTRONIC BLOOD PRESSURE GAUGE FOR MEASURING BLOOD PRESSURE BY USING VOLUME COMPENSATION METHOD

TECHNICAL FIELD

This invention relates to an electronic sphygmomanometer, and particularly to an electronic sphygmomanometer that measures blood pressure in accordance with the volume compensation method.

BACKGROUND ART

Among conventional electronic sphygmomanometers, there is a sphygmomanometer that measures blood pressure according to the oscillometric method. In the oscillometric method, an arm band (cuff) is wound around a measurement site of a measured person in advance. At the measurement time, a pressure inside the cuff (cuff pressure) is increased to become higher than a systolic blood pressure, and then, is gradually decreased. In this process of decreasing the pressure, pulsation occurring in an artery in the measurement site is detected as a pulse wave signal by a pressure sensor through the cuff. The cuff pressure and a magnitude of the detected pulsation (amplitude of the pulse wave signal) at that time are utilized to decide a systolic blood pressure and a diastolic blood pressure.

As biological information relating to blood pressure values measured in this manner, there are a degree of arteriosclerosis and vessel compliance. As techniques of finding these from a blood pressure waveform, there are a method of examining a velocity at which a pulse wave ejected from a heart is propagated (PWV: Pulse Wave Velocity) (Patent Document 1: Japanese Unexamined Patent Publication No. 2000-316821 (Japanese Patent No. 3140007), Patent Document 2: Japanese Unexamined Patent Publication No. H9-122091 (Japanese Patent No. 3599858)), and a method of examining Augmentation Index (AI), which is information of a reflected wave included in a pulse wave (Patent Document 3: Japanese Unexamined Patent Publication No. 2004-195204).

The PWV is measured in a state where sensors (cuffs or the like) that measure a pulse wave or the like at two or more positions such as in upper arms, lower legs and the like are attached as in the measurement time of an electrocardiogram and a phonocardiogram. At the measurement time, the measurement is simultaneously performed using the respective sensors. The PWV is calculated from a time difference exhibited by pulse signals detected by the respective sensors, and a length of an artery between the two points where the sensors are attached.

In this manner, since for the measurement of the PWV, the sensors such as cuffs need to be attached at two or more positions, it is difficult to measure a degree of arteriosclerosis easily and conveniently.

Moreover, the AI is calculated based on a pressure pulse wave signal measured while pressing a radial artery of a wrist with an appropriate pressure. However, a mechanism to press with the appropriate pressure, and an expensive sensor unit to precisely position a measurement site are needed, and a technique for properly attaching the sensor unit is needed. These make it difficult to measure the degree of arteriosclerosis easily and conveniently.

On the other hand, as an apparatus capable of continuously measuring a blood pressure waveform noninvasively, and being used easily and conveniently, there is a sphygmomanometer of the volume compensation method type (Patent Document 4: Japanese Examined Patent Publication No. S59-005296).

The volume compensation method is as follows. That is, it is a method in which an artery is compressed by a cuff from the outside of a biological body to keep constant a volume of the artery pulsating in synchronization with a heart rate, thereby balancing a pressure (cuff pressure) that compresses a measurement site and an internal pressure of the artery of the measurement site, that is, a blood pressure, and the cuff pressure when this balanced state is maintained is detected to thereby obtain blood pressure values continuously.

Accordingly, in the volume compensation method, two points of the detection of a volume value are important—when the artery is in an unloaded state (control target value) and the maintaining of this unloaded state (servo control). As a method of the servo control, PID (referring to control in which Proportional Control, Integral Control and Derivative Control are combined to cause the volume value to converge to the control target value) of feedback control is used.

Here, in order to perform the measurement with a high accuracy, a servo gain needs to be adjusted in accordance with a control subject. In the conventional servo control, a technique of deciding the servo gain from responsiveness to input of the control subject is common. Specifically, a method is employed in which a time required until an output value starts to respond when an input value is varied in a staircase pattern (waste time), and a velocity of change from the start of response (time constant) are measured in advance, and based on these values, the servo gain is set.

However, since this method requires adjustment through trial and error, it takes time to adjust, which makes it difficult to apply this method to the blood pressure measurement in which the control needs to quickly start.

Moreover, this method is based on the premise that the responsiveness of the control subject is unchanged, which also makes it difficult to apply the method to the control of the blood pressure measurement for a biological body whose responsiveness frequently changes in accordance with change in physical condition and the like.

Consequently, in an electronic sphygmomanometer by the volume compensation method, the control is started without performing any preadjustment, and during the control, there arises a necessity to decide an optimal servo gain. In order to decide the optimal servo gain during the control, in Patent Document 4, the servo gain is gradually increased, and utilizing the servo gain when an elimination rate of an arterial volume change signal (an amplitude during control/an amplitude before control) becomes smaller than a predetermined value, the blood pressure measurement is performed. Such control is also shown in FIG. 1 of Non-Patent Document 1 (Document 1: Yamakoshi K, Shimazu H, Togawa T, Indirect measurement of instantaneous arterial blood pressure in the rat, Am J Physiol 237, H632-H637, 1979)

Patent Document 1: Japanese Unexamined Patent Publication No. 2000-316821
Patent Document 2: Japanese Unexamined Patent Publication No. H9-122091
Patent Document 3: Japanese Unexamined Patent Publication No. 2004-195204
Patent Document 4: Japanese Examined Patent Publication No. S59-005296
Non-Patent Document 1: Yamakoshi K, Shimazu H, Togawa T, Indirect measurement of instantaneous arterial blood pressure in the rat, Am J Physiol 237, H632-H637, 1979

DISCLOSURE OF THE INVENTION

Problem to be Solved by the Invention

However, in the foregoing electronic sphygmomanometer by the conventional volume compensation method, the servo gain is decided based on the constant elimination rate of the arterial volume change signal. Accordingly, the servo gain is not adjusted for each measured person. Therefore, even when the blood pressure waveform measured in accordance with the conventional volume compensation method is used, the degree of arteriosclerosis inherent in an individual person cannot be measured.

Thus, an object of this invention is to provide an electronic sphygmomanometer capable of detecting a barometer of a degree of arteriosclerosis for each person, using a blood pressure wave measured by the volume compensation method.

Means for Solving the Problem

In order to achieve the above object, according to an aspect of this invention, there is provided an electronic sphygmomanometer to measure blood pressure in accordance with the volume compensation method, and the electronic sphygmomanometer includes: a cuff attached to a measurement site of the blood pressure; a pressure detector to detect a cuff pressure representing a pressure inside the cuff; a volume detector provided in the cuff and intended to detect an arterial volume signal indicating a volume of an artery of the measurement site; a cuff pressure adjustment unit to adjust the cuff pressure by increasing and decreasing the pressure; and a control unit.

Further, the control unit includes: a first control unit to control the cuff pressure adjustment unit and set the cuff pressure to an initial cuff pressure representing a specific pressure value; a servo control unit to servo-control the cuff pressure adjustment unit so that the volume of the artery becomes constant, based on the detected arterial volume signal after setting the cuff pressure to the initial cuff pressure; a volume change detector to detect an amount of change in the volume of the artery, based on the detected arterial volume signal, while the control by the servo control unit is being performed; an amplitude ratio detector to detect a ratio between an amplitude of the arterial volume signal detected when the cuff pressure is set to the initial cuff pressure and an amplitude of the arterial volume signal detected when the volume change detector detects that the amount of change in the volume of the artery is minimal; and an output unit to output the ratio of the amplitude detected by the amplitude ratio detector as a barometer of a degree of arteriosclerosis.

Preferably, the amplitude of the arterial volume signal detected when the cuff pressure is set to the initial cuff pressure is maximal, the servo control unit determines the arterial volume when the maximum amplitude of the arterial volume signal is detected to be a target value of the servo control, and based on a difference between the arterial volume indicated by the detected arterial volume signal and the target value, a servo gain is adjusted so that the amount of change in the volume of the artery detected by the volume change detector becomes minimal, by which the cuff pressure adjustment unit is servo-controlled by the servo control unit.

Preferably, further included is a blood pressure measurement unit to continuously measure the blood pressure while the control by the servo control unit is being performed. The blood pressure measurement unit has a decision unit to receive a detection signal from the pressure detector and decide a cuff pressure corresponding to the detection signal as the blood pressure. When the volume change detector detects that the amount of change in the volume of the artery is minimal, the blood pressure decided by the decision unit is outputted by the blood pressure measurement unit.

Preferably, in accordance with a correlationship between the ratio of the amplitude and the degree of arteriosclerosis, the control unit detects a degree of arteriosclerosis of the measurement site, based on the ratio of the amplitude detected by the amplitude ratio detector.

Preferably, in a process of increasing the servo gain at a constant rate by the servo control unit, when the amount of change in the volume of the artery detected by the volume change detector converges, the amplitude ratio detector detects the ratio of the amplitude.

Preferably, when it is detected that the amount of change in the volume of the artery detected by the volume change detector has a predetermined value or less, detected is that the amount of change in the volume of the artery is converged.

Preferably, a difference between the amount of change in the volume of the artery in one pulse and the amount of change in the volume of the artery one pulse ahead is detected in each pulse of a pulse wave of the detected arterial volume signal. When it is detected continuously in a plurality of pulses that the detected difference indicates a predetermined value or less, detected is that the amount of change in the volume of the artery is converged.

Preferably, in the process of increasing the servo gain at the constant rate by the servo control unit, when a control error in one pulse of the pulse wave becomes minimal, detected is that the amount of change in volume of the artery has converged, and the control error indicates a difference between the arterial volume indicated by the detected arterial volume signal and the target value.

Preferably, in the process of increasing the servo gain at the constant distance by the servo control unit, when a magnitude of the pulsation indicated by the cuff pressure by the servo control converges, detected is that the amount of change in the volume of the artery is converged. The magnitude of the pulsation indicated by the cuff pressure indicates an amplitude level of the cuff pressure signal indicating the change in the cuff pressure detected by the pressure detector.

Effect of the Invention

According to the present invention, the electronic sphygmomanometer that measures the blood pressure in accordance with the volume compensation method decides a control value for the servo control at the time of blood pressure measurement in accordance with change in volume of an artery inherent to an individual measured person, which is detected in a process in which a cuff pressure pressing to a measurement site is adjusted. At this time, a barometer of a degree of arteriosclerosis is detected as a ratio of an amplitude of an arterial volume signal. Accordingly, the barometer of the degree of arteriosclerosis can be obtained as one representing a property of the artery of the individual measured person.

Figure 1:
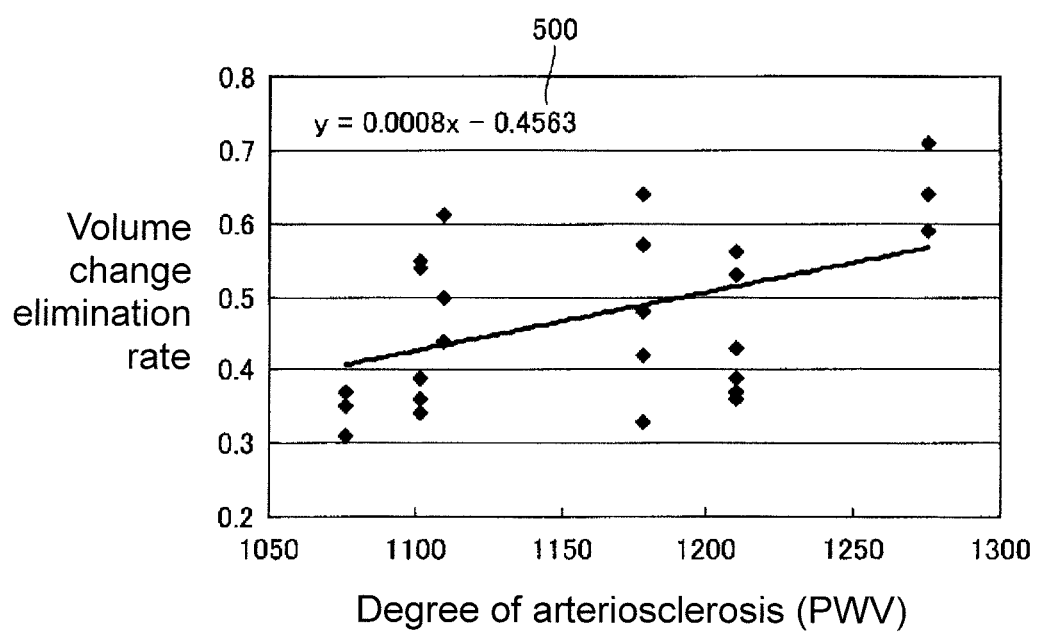
FIG. 1 is a diagram showing a correlationship between a volume change elimination rate and a degree of arteriosclerosis based on an experiment result.

DESCRIPTION OF SYMBOLS 1 electronic sphygmomanometer
102 control target value detector
104 cuff pressure setting unit
106 servo control unit
108 blood pressure decision unit
109 gain decision unit
110 volume change elimination rate calculating unit
111 arteriosclerosis degree calculating unit

BEST MODE FOR CARRYING OUT THE INVENTION

Hereinafter, referring to the drawings, embodiments of this invention are described in detail. The same symbols designate the same or corresponding portions in the figures, and descriptions thereof are not repeated.

In an electronic sphygmomanometer using the volume compensation method according to the respective embodiments, a servo gain for blood pressure measurement is decided by focusing attention on a fact that a volume change elimination rate differs depending on an elastic property of an artery, that is, a degree of arteriosclerosis. Specifically, as the artery becomes harder, responsiveness to pressing force becomes worse, thereby making the control difficult, and increasing an amplitude of a pulse wave signal during control. As a result, the volume change elimination rate becomes a large value. On the contrary, as the artery becomes softer, the elimination rate becomes a smaller value. Consequently, the inventors have achieved a suggestion that the value of the volume change elimination rate can be calculated as a barometer of the degree of arteriosclerosis.

The inventors conducted experiments based on this suggestion, and could obtain data indicating a correlationship between the volume change elimination rate and the degree of arteriosclerosis shown in FIG. 1. In FIG. 1, if in a two-dimensional coordinate plane, a Y axis indicates the volume change elimination rate and an X axis indicates the degree of arteriosclerosis expressed by PWV, the correlationship of both is approximately expressed by a linear function indicated by an expression 500. This allowed the inventors to recognize that the volume change elimination rate has a proportional relation to the elastic property (hardness) of the artery, and to achieve a finding that a barometer of the degree of arteriosclerosis (volume change elimination rate) can be detected using the volume change elimination rate. Experimental data of FIG. 1 is data obtained by measuring a blood vessel in an invasive state.

Furthermore, in the volume compensation method, the inventors achieved the following finding as to decision of the servo gain according to servo control to maintain an unloaded state of the artery.

As the servo gain is increased, an amplitude of an arterial volume change signal gradually becomes smaller, and converges to a minimum value. That is, in a process in which the servo gain is increased by the servo control, a magnitude of pulsation detected from a cuff pressure signal also converges, so that an amount of change in volume of the artery converges. If the servo gain is increased more, a control system becomes unstable, thereby causing unnecessary vibration of high frequency components in a control signal. By its nature, further increasing the gain causes abnormal oscillation in the control signal, resulting in inability of control. Consequently, utilizing this nature, the inventors achieved a finding that a point where the amplitude of the arterial volume change signal become minimal is detected in the process in which the servo control is performed while increasing the servo gain, by which an optimal servo gain for maintaining the unloaded state of the artery can be decided for each person, and the barometer of the degree of arteriosclerosis inherent to each person can be detected by the volume change elimination rate detected at that time.

Hereinafter, an electronic sphygmomanometer that measures the blood pressure using the volume compensation method according to each of the embodiments is described. The blood pressure measurement using the volume compensation method utilizes a procedure disclosed in Patent Document 4 (Japanese Examined Patent Publication No. S59-005296).

The electronic sphygmomanometer according to each of the embodiments continuously measures the blood pressure by the volume compensation method. The electronic sphygmomanometer performs feedback control so as to constantly balance a biological external pressure and an arterial internal pressure, that is, blood pressure. In other words, the electronic sphygmomanometer performs fine adjustment of a cuff pressure so as to maintain an arterial wall in an unloaded state, and the biological external pressure at that time (in the unloaded state) is measured to thereby measure the blood pressure continuously.

First Embodiment

Figure 2:
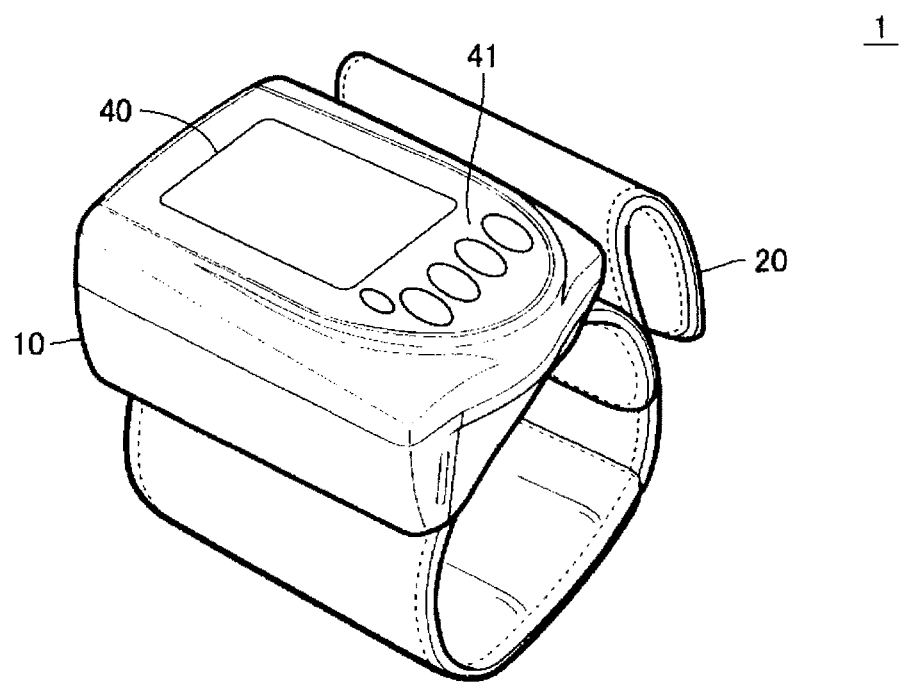
FIG. 2 is an external perspective diagram of an electronic sphygmomanometer according to a first embodiment of the present invention.

FIG. 2 is an external perspective diagram of an electronic sphygmomanometer 1 according to a first embodiment of the present invention.

Referring to FIG. 2, the electronic sphygmomanometer 1 includes a main body portion 10, and a cuff 20 that can be wound around extremities of a measured person. The main body portion 10 is mounted on the cuff 20. In a surface of the main body portion 10, a display unit 40 made of, for example, liquid crystal or the like, and an operation unit 41 to receive an instruction from a user (measured person) are arranged. The operation unit 41 includes a plurality of switches.

In the present embodiment, the "extremities" indicates sites excluding fingers or toes in upper limbs and lower limbs. That is, the extremities include a site from a wrist to a base of an arm and a site from an ankle to a base of a leg. In the following description, the cuff 20 is attached to a wrist of the measured person.

As to the electronic sphygmomanometer 1 in the present embodiment, while a form in which the main body portion 10 is mounted on the cuff 20, as shown in FIG. 2, is described as one example, as in an upper-arm type sphygmomanometer, a form in which the main body portion 10 and the cuff 20 are connected by an air tube (air tube 31 in FIG. 4 described later) may also be employed.

Figure 3:
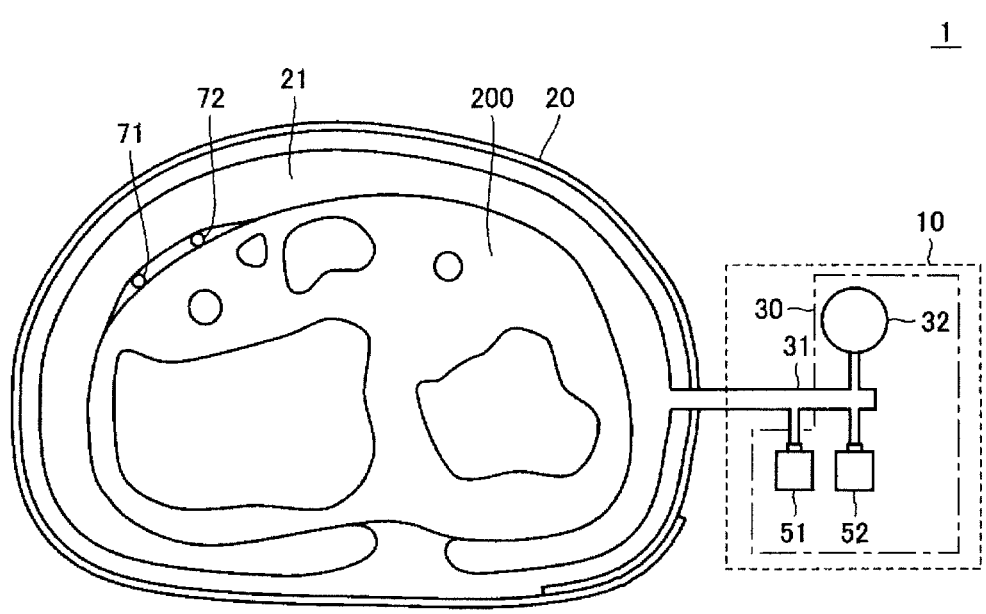
FIG. 3 is diagram representing a concept of controlling a cuff pressure for blood pressure measurement in the electronic sphygmomanometer according to the first embodiment of the present invention.

FIG. 3 is a diagram representing a concept of controlling the cuff pressure for the blood pressure measurement in the electronic sphygmomanometer 1 according to the first embodiment of the present invention. FIG. 3 shows a state where the cuff 20 is attached to a wrist 200 of the measured person.

Referring to FIG. 3, in the main body portion 10, an adjustment mechanism of the cuff pressure including a pump 51 and an exhaust valve (hereinafter, simply referred to as a "valve") 52 is arranged.

An air system 30 made up of the pump 51, the valve 52 and a pressure sensor 32 to detect a pressure (cuff pressure) inside an air bladder 21 is connected to the air bladder 21 contained inside the cuff 20 through the air tube 31. In this manner, since the air system 30 is provided in the main body portion 10, thickness of the cuff 20 can be kept thin.

Inside of the air bladder 21, light emitting elements 71 and light receiving element 72 are arranged at predetermined intervals. While in the present embodiment, the light emitting elements 71 and the light receiving elements 72 are arrayed along a circumference of the wrist in the state where the cuff 20 is attached, the present invention is not limited to the above-described arrangement example.

Figure 4:
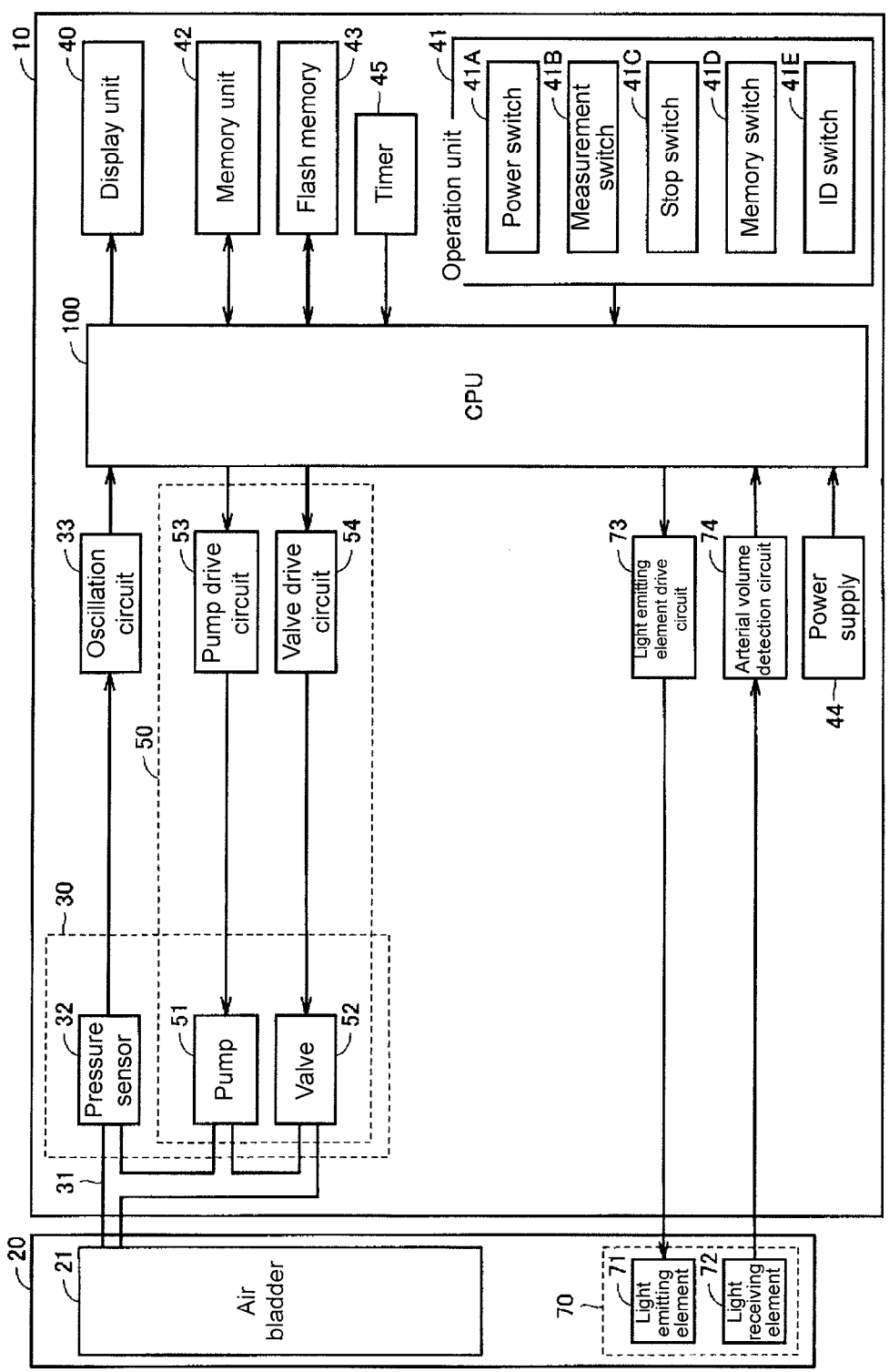
FIG. 4 is a block diagram representing a hardware configuration of the electronic sphygmomanometer according to the first embodiment of the present invention.

FIG. 4 is a block diagram representing a hardware configuration of the electronic sphygmomanometer 1 according to the first embodiment of the present invention.

Referring to FIG. 4, the cuff 20 of the electronic sphygmomanometer 1 includes the air bladder 21 and an arterial volume sensor 70. The arterial volume sensor 70 has above-described the light emitting elements 71 and the light receiving elements 72. The light emitting elements 72 irradiate light to the artery, and the light receiving elements 72 receives light transmitted through, or reflected at the artery of the light irradiated by the light emitting elements 71.

The arterial volume sensor 70 only needs to detect a volume of the artery, and may detect the volume of the artery by impedance. In this case, in place of the light emitting elements 71 and the light receiving elements 72, a plurality of electrodes to detect an impedance of a site including the artery are included.

The main body portion 10 includes, in addition to the above-described display unit 40 and the operation unit 41, a CPU (Central Processing Unit) 100 to intensively control the respective units and perform various arithmetic operations, a memory unit 42 to store programs that causes the CPU 100 to perform predetermined operations and various type of data, a nonvolatile memory to store measured blood pressure data in accordance with FIG. 5 described later, for example, a flash memory 43, a power supply 44 to supply power to the respective units through the CPU 100, and a timer unit 45 that measures a current time and outputs the timing data to the CPU 100. The operation unit 41 has a power switch 41A to receive input of an instruction to power on or off, a measurement switch 41B to receive an instruction of measurement start, a stop switch 41C to receive an instruction of measurement stop, a memory switch 41D to receive an instruction to read information such as the blood pressure recorded on the flash memory 43, and ID switch 41E operated to input an ID (identifier) information for identifying the measured person.

The main body portion 10 further includes the above-described air system 30, an adjustment mechanism 50 of the cuff pressure, an oscillation circuit 33, a light emitting element drive circuit 73, and an arterial volume detection circuit 74.

The adjustment mechanism 50 has, in addition to the pump 51 and the valve 52, a pump drive circuit 53 and a valve drive circuit 54.

The pump 51 supplies air to the air bladder 21 to increase the cuff pressure. The valve 52 is opened or closed to exhaust or fill the air in the air bladder 21. The pump drive circuit 53 controls the driving of the pump 51 based on a control signal given from the CPU 100. The valve drive circuit 54 performs the opening and closing control of the valve 52 based on a control signal given from the CPU 100.

The light emitting element drive circuit 73 causes the light emitting elements 71 to emit light at predetermined timing in accordance with an instruction signal from the CPU 100. The arterial volume detection circuit 74 detects an arterial volume, based on a signal from the light receiving elements 72.

The pressure sensor 32 is a capacitance type pressure sensor, in which a volume value changes in accordance with the cuff pressure. The oscillation circuit 33 outputs a signal of an oscillation frequency in accordance with the volume value of the pressure sensor 32 to the CPU 100. The CPU 100 senses a pressure by converting the signal obtained from the oscillation circuit 33 to the pressure.

Figure 6:
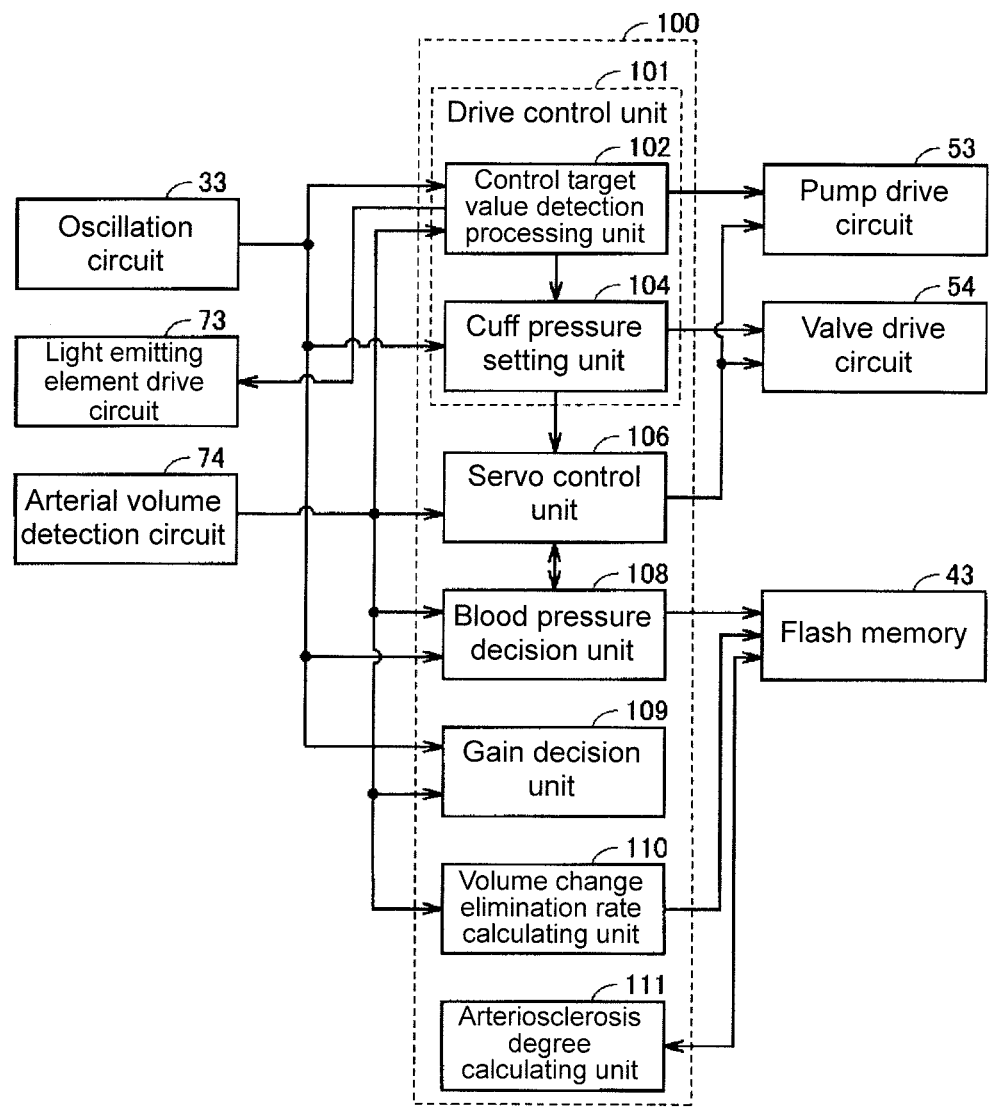
FIG. 6 is a functional block diagram showing a functional configuration of the electronic sphygmomanometer according to the first embodiment of the present invention.

FIG. 6 is a functional block diagram showing a functional configuration of the electronic sphygmomanometer 1 according to the first embodiment of the present invention.

Referring to FIG. 6, the CPU 100 includes a drive control unit 101 that performs control to set the cuff pressure to an initial cuff pressure, a servo control unit 106 that performs feedback control to continuously measure the blood pressure, a blood pressure decision unit 108, a gain decision unit 109 to decide a gain relating to the servo control, a volume change elimination rate calculating unit 110 that calculates the volume change elimination rate, and an arteriosclerosis degree calculating unit 111 to calculate the degree of arteriosclerosis based on the calculated volume change elimination rate. In FIG. 6, for ease of description, only peripheral hardware that directly communicates signals with these respective units that the CPU 100 has is shown.

The drive control unit 101 includes a control target value detector 102 to detect a control target value for the servo control, and a cuff pressure setting unit 104 to set the cuff pressure.

The control target value detector 102 performs processing of deriving the initial cuff pressure in a process in which the cuff pressure is increased up to a predetermined value (e.g., 200 mmHg). The control target value detector 102 causes the pump drive circuit 53 to drive the pump 51, and causes the light emitting element drive circuit 73 to drive the light emitting elements 71. Driving the pump 51 gradually increases the cuff pressure. The driving of the light emitting elements 71 allows the signal received by the light-receiving elements 72 to be outputted to the arterial volume detection circuit 74. The control target value detector 102 inputs the volume change signal indicating change (amplitude) in each pulse of an arterial volume signal outputted from the arterial volume detection circuit 74.

The control target value detector 102 controls the driving of the pump drive circuit 53 until the cuff pressure becomes a predetermined value. A (tentative) maximum value of the volume change signal is detected until the cuff pressure reaches the predetermined value, and the signal from the oscillation circuit 33 is inputted to convert the inputted signal to a pressure value. The detected tentative maximum value and the cuff pressure at this time point are recorded on a predetermined area of the flash memory 43. The tentative maximum value and the cuff pressure may be recorded so as to be overwritten every time the recorded (tentative) maximum value is updated.

Eventually, a value recorded as the maximum value of the volume change signal is determined to be the control target value at the time of servo control. Moreover, the cuff pressure when the volume change signal has a maximum value (reference cuff pressure at the time of servo control) is determined to be the initial cuff pressure.

The control target value detector 102, when sensing that the cuff pressure has become the predetermined value, stops the driving of the pump drive circuit 53. The determined initial cuff pressure and control target value are outputted to the cuff pressure setting unit 104.

The reference cuff pressure as the initial cuff pressure may be derived in a process where the cuff pressure is decreased from the predetermined value.

The cuff pressure setting unit 104 has the signal from the oscillation circuit 33 inputted, and drives the valve drive circuit 54 until the cuff pressure becomes the initial cuff pressure. This allows the valve 52 to exhaust the air and the cuff pressure is decreased from the cuff pressure of the predetermined value to the initial cuff pressure.

The servo control unit 106 drives the light emitting element drive circuit 73. The servo control unit 106 controls the pump drive circuit 53 and the valve drive circuit 54 so as to make the volume of the artery constant, based on the signal from the arterial volume detection circuit 74.

More specifically, the servo control unit 106 controls the pump drive circuit 53 or the valve drive circuit 54 so that a difference between the arterial volume signal received from the arterial volume detection circuit 74, and the control target value is minimal (preferably, zero). That is, the pump drive circuit 53 or the valve drive circuit 54 controls the operation of the pump 51 or the opening and closing of the valve 52 so that the value (amplitude) of the volume change signal is not larger than a predetermined threshold.

The blood pressure decision unit 108 continuously (periodically) receives the signal inputted from the oscillation circuit 33 (referred to as a "pressure detection signal") when the control by the servo control unit 106 is performed, and performs processing for deciding the cuff pressure corresponding to the pressure detection signal as the blood pressure.

More specifically, the blood pressure decision unit 108 determines whether or not the difference between the value of the arterial volume signal and the control target value is not larger than the threshold. Only when it is not larger than the threshold, the cuff pressure at that time is decided as the blood pressure. The decided blood pressure is stored in chronological order in the flash memory 43.

The operations of the respective functional blocks included in the CPU 100 may be realized by executing software stored in the memory unit 42, or at least one of these functional blocks may be realized as hardware.

Alternatively, at least one of the blocks described as hardware (circuits) may be realized by the CPU 100 executing software stored in the memory unit 42.

Next, operation of the electronic sphygmomanometer 1 in the present first embodiment is described.

Figure 7:
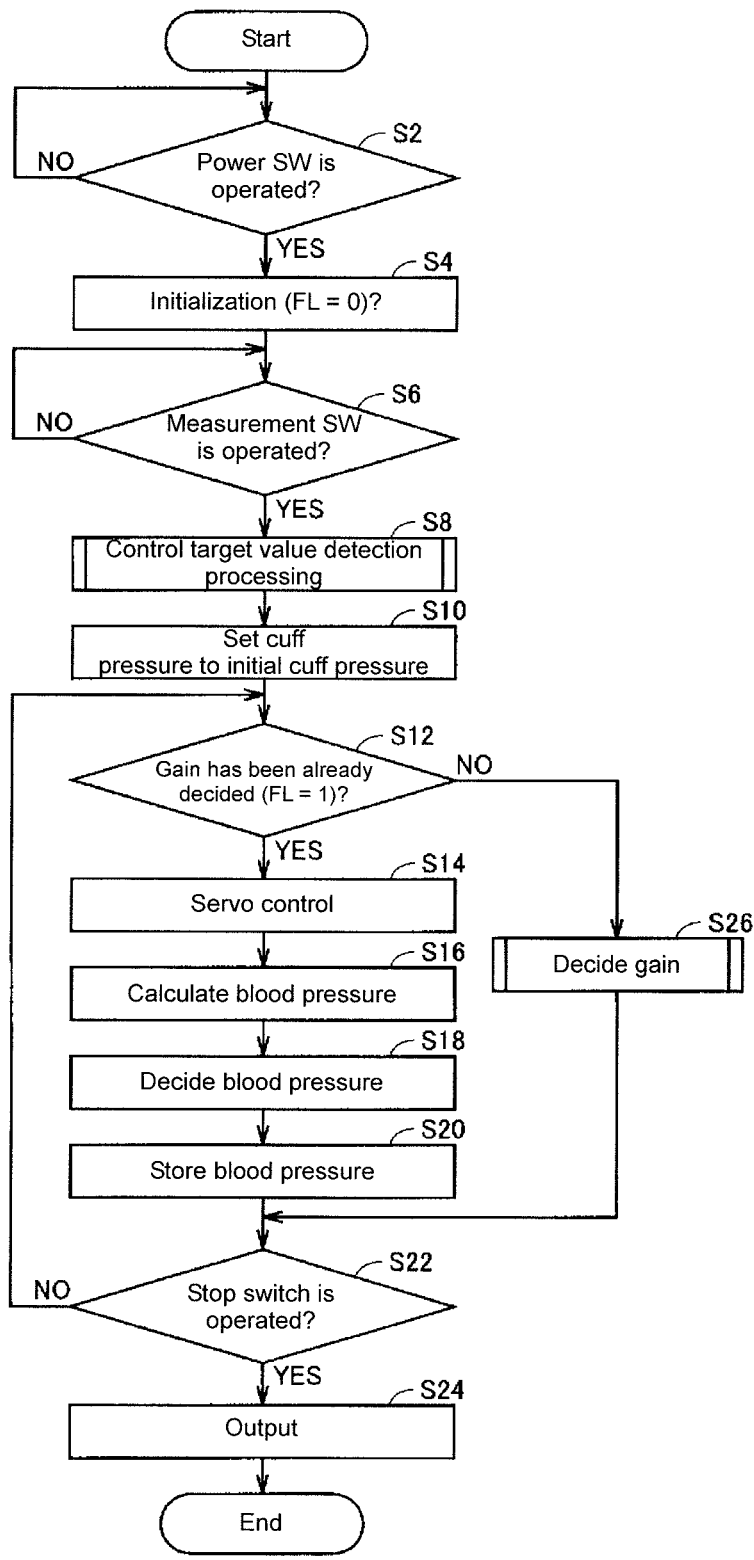
FIG. 7 is a flowchart showing blood pressure measurement processing in the first embodiment of the present invention.

FIG. 7 is a flowchart showing blood pressure measurement processing in the first embodiment of the present invention. The processing shown in the flowchart of FIG. 7 is stored in the memory unit 42 as a program in advance, and the CPU 100 reads and executes this program to thereby realize the function of the blood pressure measurement processing. It is assumed that the measured person wears the cuff 20 of the electronic sphygmomanometer 1 around his or her wrist, which is a measurement site, as shown in FIG. 3 when the blood pressure measurement is performed.

Referring to FIG. 7, the CPU 100 determines whether or not the power switch 41A is operated (e.g., pressed) (step S2). If the CPU 100 determines that the power switch 41A is operated (YES in step S2), the processing goes to step S4.

In step S4, the CPU 100 performs initialization processing. Specifically, a predetermined area of the memory unit 42 is initialized, the air in the air bladder 21 is exhausted, and correction of the pressure sensor 32 is performed. At this time, a value of a flag FL to instruct whether or not the gain for the servo control is decided is initialized. For instance, the value of the flag FL is updated to 0. The flag FL is a temporary variable prepared for the flowchart, and points to a predetermined storage area of an internal memory not shown of the CPU 100.

When the initialization is ended, the CPU 100 determines whether or not the measurement switch 41B is operated (e.g., pressed) (step S6). The CPU 100 stands by until the measurement switch 41B is operated. If the CPU 100 determines that the measurement switch 41B is pressed (YES in step S6), the processing goes to step S8.

In step S8, the control target value detector 102 executes the processing of detection of the initial cuff pressure and the control target value. The detection of the initial cuff pressure and the control target value are performed as follows.

An arterial volume signal (a DC component of the volume pulse wave signal) PGdc at that time, and an arterial volume change signal (an AC component of the volume pulse wave signal) PGac are detected while the cuff pressure is gradually increased. These signals are detected by the arterial volume detection circuit 74. That is, the arterial volume detection circuit 74 has an HPF (High Pass Filter) circuit not shown.

In the operation, when the volume pulse signal indicating the change in volume of the artery is inputted from the arterial volume sensor 70, the input signal is split by the HPF circuit into the arterial volume signal PGdc of the DC component of the volume pulse wave signal and the arterial volume change signal PGac of the AC component thereof to be outputted. For instance, if a filter constant is 1 Hz, the signal of 1 Hz or lower is derived as the DC component, and the signal beyond 1 Hz is derived as the AC component. The control target value detector 102 inputs the arterial volume signal PGdc and the arterial volume change signal PGac.

The control target value detector 102 determines whether a level of the arterial volume change signal PGac currently detected is maximal, and a level value of the arterial volume signal PGac, a value of the arterial volume signal PGdc and the cuff pressure detected at that time are associated with one another and are stored in a predetermined memory area. This operation is repeated until the cuff pressure reaches a predetermined pressure. This predetermined pressure is instructed by cuff pressure data PC1 read from the flash memory 43 (e.g., 200 mmHg).

The arterial volume signal PGdc associated with the maximum value of the values of the arterial volume change signal PGac stored in the predetermined memory area when it is detected that the cuff pressure has reached the predetermined pressure is determined to be the control target value, and the cuff pressure stored in association is determined to be the control initial cuff pressure. This allows the control target value and the initial cuff pressure to be detected.

Figure 8:
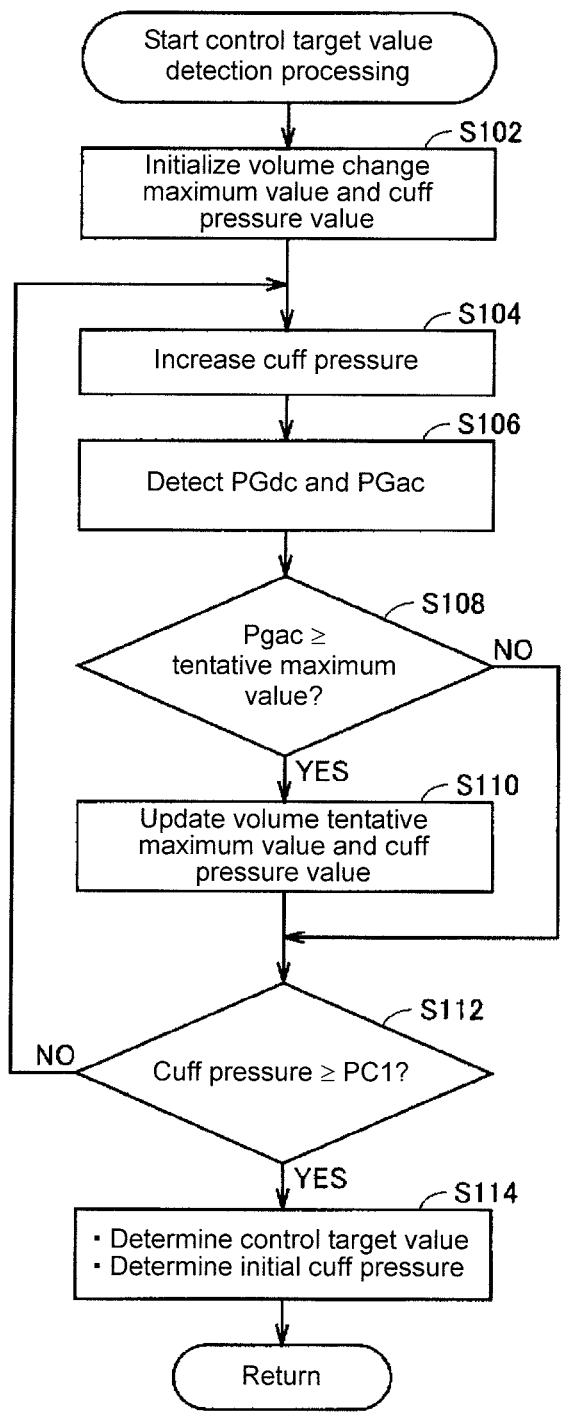
FIG. 8 is a flowchart showing detection processing of a control target value and an initial cuff pressure in the first embodiment of the present invention.
Figure 9:
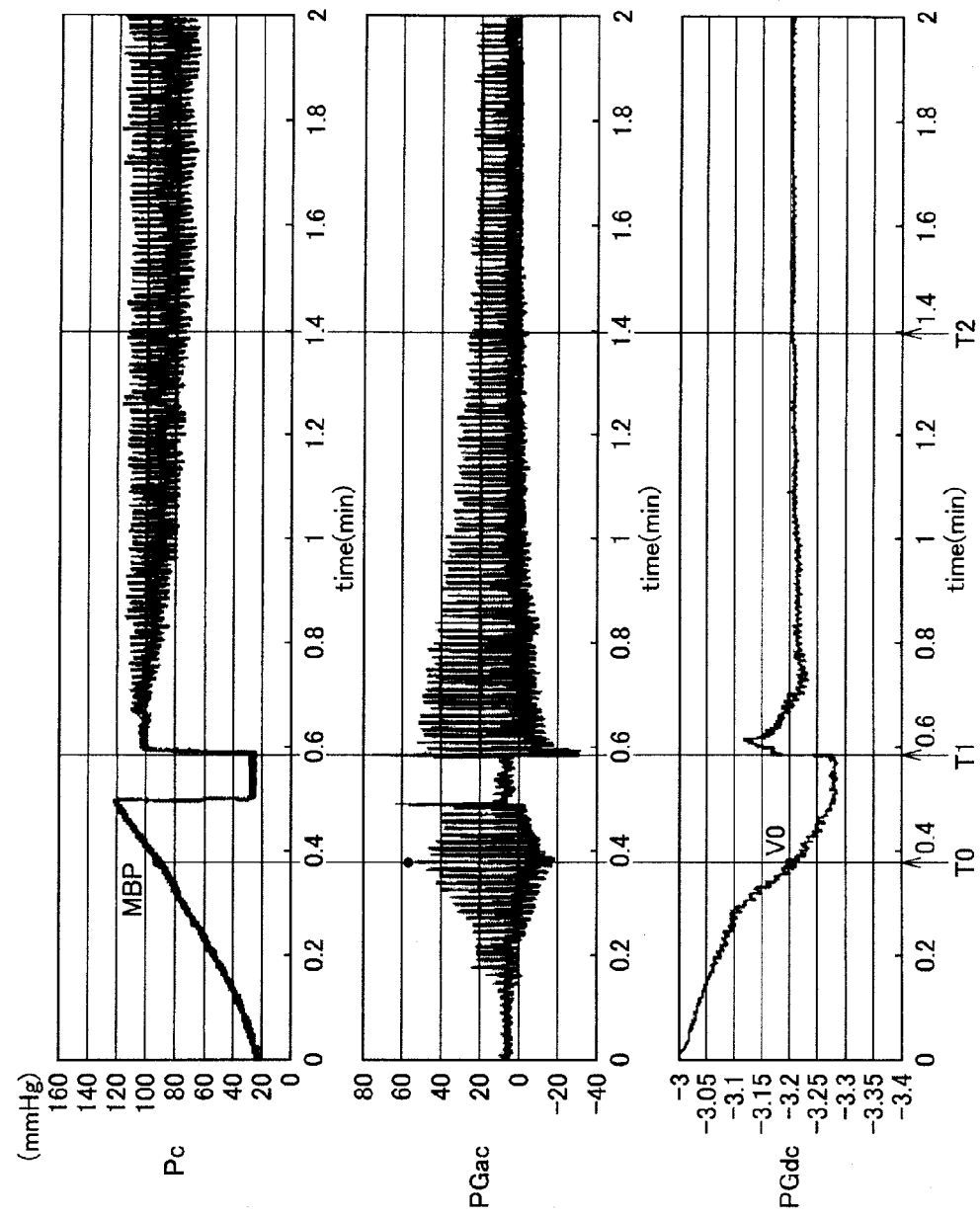
FIG. 9 is a diagram for explaining the blood pressure measurement processing in the first embodiment of the present invention.

The above-described detection of the control target value and the initial cuff pressure is described in detail, using FIGS. 8 and 9.

FIG. 8 is a flowchart showing the detection processing of the control target value and the initial cuff pressure in the first embodiment of the present invention. FIG. 9 is a diagram for explaining the blood pressure measurement processing of the first embodiment of the present invention. At the upper stage of FIG. 9, a signal indicating a cuff pressure Pc detected by the pressure sensor 32 is shown along a time axis that the timer 45 measures. At the intermediate and lower stages of FIG. 9, the arterial volume change signal PGac and the arterial volume signal PGdc are shown along the same time axis.

Referring to FIG. 8, the control target value detector 102 initializes the maximum value of the arterial volume change signal PGac and the cuff pressure value stored in the predetermined area of the memory unit 42 (step S102). In the following processing, the maximum value of the arterial volume change signal PGac is updated as needed, and thus, a value until the maximum value is finally determined is referred to as a "volume tentative maximum value".

Next, the pump drive circuit 53 is controlled to increase the cuff pressure (step S104).

At the stage where the cuff pressure is increased, the control target value detector 102 detects the arterial volume signal PGdc and the arterial volume change signal PGac, based on the volume pulse wave signal inputted from the arterial volume detection circuit 74 (step S106).

The control target value detector 102 determines whether or not the value of the arterial volume change signal PGac is not less than the volume tentative maximum value stored in the memory unit 42 (step S108). If it is determined that the value of the arterial volume change signal PGac is not less than the volume tentative maximum value (YES in step S108), the processing goes to step S110. On the other hand, if it is determined that the arterial volume change signal PGac is lower than the volume tentative maximum value (NO in step S108), then the processing goes to step S112.

In step S110, the control target value detector 102 updates the volume tentative maximum value and records the cuff pressure at that time point so as to overwrite. When this processing ends, the processing is moved to step S112.

In step S112, the control target value detector 102 determines whether or not the detected cuff pressure Pc indicates the cuff pressure of the predetermined value PC1 or higher. If it is determined that the cuff pressure Pc does not indicate the cuff pressure of the predetermine value PC1 or higher (NO in step S112), the processing returns to step S104. On the other hand, if it is determined that the cuff pressure Pc indicates the cuff pressure of the predetermined value PC1 or higher (YES in step S112), then the processing goes to step S114.

In step S114, the control target value detector 102 determines the volume tentative maximum value finally recorded in step S110 to be the maximum value, and the value of the cuff pressure Pc detected at a time T0 when the maximum value is detected is determined to be the initial cuff pressure (cuff pressure pointed by a symbol MBP in FIG. 9). The control target value detector 102 further determines the value of the arterial volume signal PGdc stored in association with the arterial volume change signal PGac at the time T0 to be a control target value V0.

When the processing in step S114 ends, the processing is returned to a main routine.

Referring again to FIG. 7, when the detection processing of the control target value and the initial cuff pressure as described above ends, the cuff pressure setting unit 104 controls the valve drive circuit 54, and sets the cuff pressure Pc to the initial cuff pressure (step S10). Referring to FIG. 9, the cuff pressure setting unit 104 stops the valve drive circuit 54 at a time T1 when the cuff pressure Pc is set to the initial cuff pressure.

Once the cuff pressure is set to the initial cuff pressure in this manner, an amplitude that the arterial volume change signal PGac exhibits becomes maximal.

When the cuff pressure is set to the initial cuff pressure, gain decision processing (step S26) is performed until an optimal gain of the servo control is decided (NO in step S12). The detection as to whether or not the optimal gain has been decided in step S12 is performed in accordance with the value of the flag FL. Specifically, if it is determined that the value of flag FL instructs 1, it is detected that the optimal gain has been decided (YES in step S12), and if not (NO in step S12), it is detected that the optimal gain has not been decided, and the processing moves to the processing for deciding the optimal gain by the gain decision unit 109 (step S26). A procedure of the gain decision by the gain decision unit 109 will be described later.

If the optimal gain has been decided by the gain decision unit 109 (YES in step S12), arterial volume constant control by the servo control unit 106 is executed, using the decided gain (step S14). Specifically, the servo control unit 106 has the arterial volume signal PGdc and the arterial volume change signal PGac inputted from the arterial volume detection circuit 74, and outputs the control signals to the pump drive circuit 53 and the valve drive circuit 54 to drive the pump 51 and the valve 52. The pump 51 and the valve 52 are driven so that the difference between the level of the detected arterial volume signal PGdc and the control target value V0 becomes minimal.

The control signals of the pump 51 and the valve 52 are calculated from a value obtained by multiplying the difference between the level of the arterial volume signal PGdc and the control target value V0 by the servo gain. If the servo gain is increased, the pulsation indicated by the cuff pressure is increased by the servo control. That is, in the present embodiment, the servo gain means a coefficient for deciding a magnitude of the pulsation of the cuff pressure by the servo control.

In the example of FIG. 9, it is shown that the arterial volume constant control (servo control) is started at a time T2. The gain decision processing is performed in a period from the time T1 to T2.

In parallel to the above-described arterial volume constant control, the blood pressure decision unit 108 executes processing of blood pressure calculation and blood pressure decision (steps S16 and S18). Specifically, the cuff pressure Pc detected while the arterial volume constant control is being performed is decided as blood pressure (step S18).

Data of the decided blood pressure is stored in the flash memory 43 (step S20). When the processing in step S20 ends, the processing moves to step S22.

At the time T2 or later shown in FIG. 9, the difference between the arterial volume and the control target value V0 is nearly zero by the servo control using the decided gain. That is, the artery is maintained in the unloaded state by the servo control unit 106. Accordingly, the cuff pressure Pc detected at the time T2 or later is decided as the blood pressure. That is, a maximum value and a minimum value of the amplitude in each pulse of the signal indicating the cuff pressure Pc are detected by differential processing of the waveform of the signal or the like, so that the detected maximum value is calculated as the equivalent of a systolic blood pressure and the minimum value is calculated as the equivalent of a diastolic blood pressure.

Subsequently, in step S22, the servo control unit 106 determines whether or not the stop switch 41C is operated (e.g., pressed). If it is determined that the stop switch 41C is not operated (No in step S22), the processing returns to step S12. If it is determined that the stop switch 41C is operated (YES in step S22), then the measured blood pressure data is stored in the flash memory 43, and displayed on the display unit 40 (step S24). This allows the series of blood pressure measurement processing to end.

While in the present embodiment, when the operation of the stop switch 41C is sensed, the blood pressure measurement processing ends, after a predetermined time has been elapsed since the arterial volume constant control was started, it may end.

Figure 10:
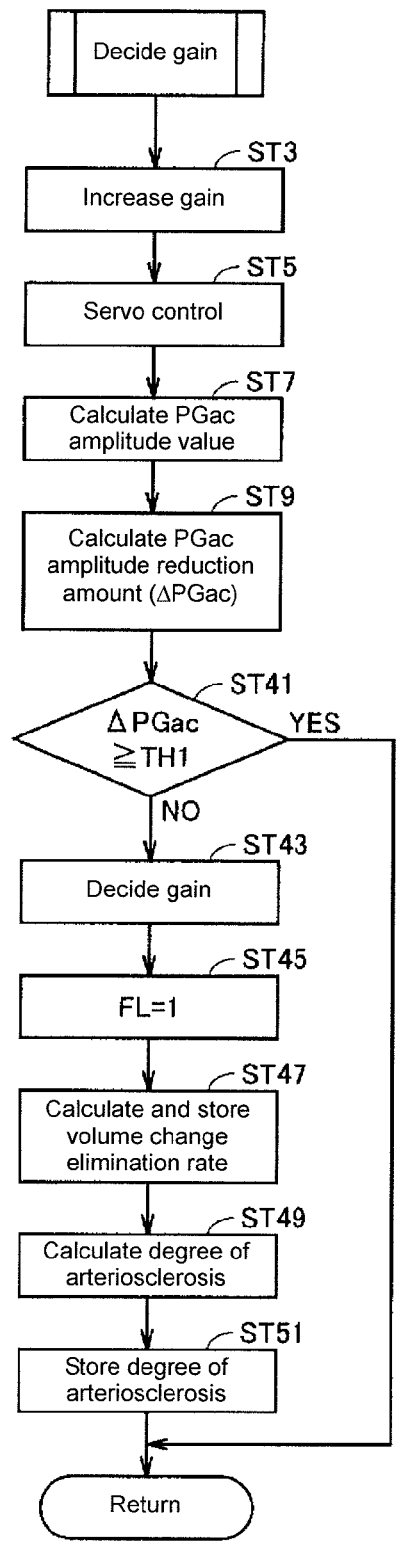
FIG. 10 is a flowchart of gain decision processing according to the first embodiment of the present invention.

Next, the gain decision processing (step S26) according to the present first embodiment is described in accordance with a flowchart in FIG. 10. In the present first embodiment is known a property that as the servo gain is increased at a constant rate, the amplitude of the arterial volume change signal PGac largely reduces at the beginning, but a reduction amount gradually becomes small, and the amplitude converges to a certain value. Utilizing this property, a convergence point of the amplitude of the arterial volume change signal PGac is detected to thereby decide the optimal servo gain.

First, the servo control unit 106 increases the servo gain at a constant rate (step ST3).

Subsequently, the servo control unit 106 performs the servo control using this servo gain (step ST5). The gain decision unit 109 detects the amplitude value in each pulse, based on the detected arterial volume change signal PGac (step ST7), and calculates an amplitude reduction amount ΔPGac (ΔPGac=an amplitude level of the arterial volume change signal PGac one pulse ahead–a current amplitude level of the arterial volume change signal PGac) (step ST9). Data of the calculated amplitude reduction amount ΔPGac and the amplitude level of the arterial volume change signal PGac in each pulse are stored in the internal memory of the CPU 100. The amplitude level of the arterial volume change signal PGac, for example, corresponds to a maximum value calculated by extracting a waveform of the arterial volume change signal PGac in one pulse and subjecting the extracted waveform to differential processing.

When the gain decision unit 109 continuously detects that the amplitude reduction amount ΔPGac becomes smaller than a predetermined threshold TH1 (NO in step ST41), it determines that the arterial volume change signal PGac has converged, and decides a value at this time point as the servo gain for use in the blood pressure calculation processing (step ST43). Since the decided servo gain is given to the servo control unit 106, the servo control unit 106 can perform the servo control based on the given gain.

In order to instruct that the gain has been decided, 1 is set in the flag FL (step ST45). The volume change elimination rate calculating unit 110 calculates the volume change elimination rate (the current amplitude level of the arterial volume change signal PGac/the amplitude level of the arterial volume change signal PGac detected when the cuff pressure is set to the initial cuff pressure) at this time point in each pulse of the arterial volume change signal PGac, and stores the same in the flash memory 43 (step ST47). The amplitude level of the arterial volume change signal PGac detected when the cuff pressure is set to the initial cuff pressure is assumed to have been stored in the internal memory of the CPU 100.

Next, the arteriosclerosis degree calculating unit 111 reads, from the flash memory 43, the volume change elimination rate calculated previously, and based on the read volume change elimination rate, the degree of arteriosclerosis (PWV) is calculated, using the expression 500 of the correlationship shown in FIG. 1 (step ST49). The calculated degree of arteriosclerosis is stored in the flash memory 43 (step ST51).

The calculated volume change elimination rate is displayed on the display unit 40 as a barometer of the degree of arteriosclerosis. At this time, the volume change elimination rate as the barometer of the degree of arteriosclerosis may be displayed together with the calculated blood pressure values, or may be displayed on the display unit 40 separately from the calculated blood pressure values. Moreover, in order to promote easy understanding of the relationship with the degree of arteriosclerosis, for example, the calculated volume change elimination rate may be converted to the degree of arteriosclerosis (PWV) in accordance with the relationship or the expression 500 shown in FIG. 1, and the degree of arteriosclerosis (PWV) obtained by the conversion may be displayed. Furthermore, statistical data based on the statistical materials, in which the data of the degree of arteriosclerosis (PWV) and corresponding average blood vessel ages are associated with one another, is stored in the memory unit 42 in advance, and by searching the statistical data based on the obtained degree of arteriosclerosis (PWV), the data of the corresponding average blood vessel age may be read and displayed on the display unit 40.

The above-described procedure allows the processing of the gain decision (step S26) according to the present first embodiment to end.

The foregoing threshold TH1 is a value decided in advance by sampling from a number of subjects, and for example, a value that is 10% of the maximum value of the amplitude of the arterial volume change signal PGac can be used.

In this manner, in the process in which the servo gain is increased at a constant rate by the servo control unit 106, it can be detected that the change amount of the arterial volume converges when a magnitude of pulsation that the artery of the measurement site exhibits in synchronization with the heart rate, that is, the amplitude that the arterial volume change signal PGac exhibits converges to the threshold TH1.

A structure of measurement data stored in the flash memory 43 by the above-described blood pressure measurement processing is described.

Figure 5:
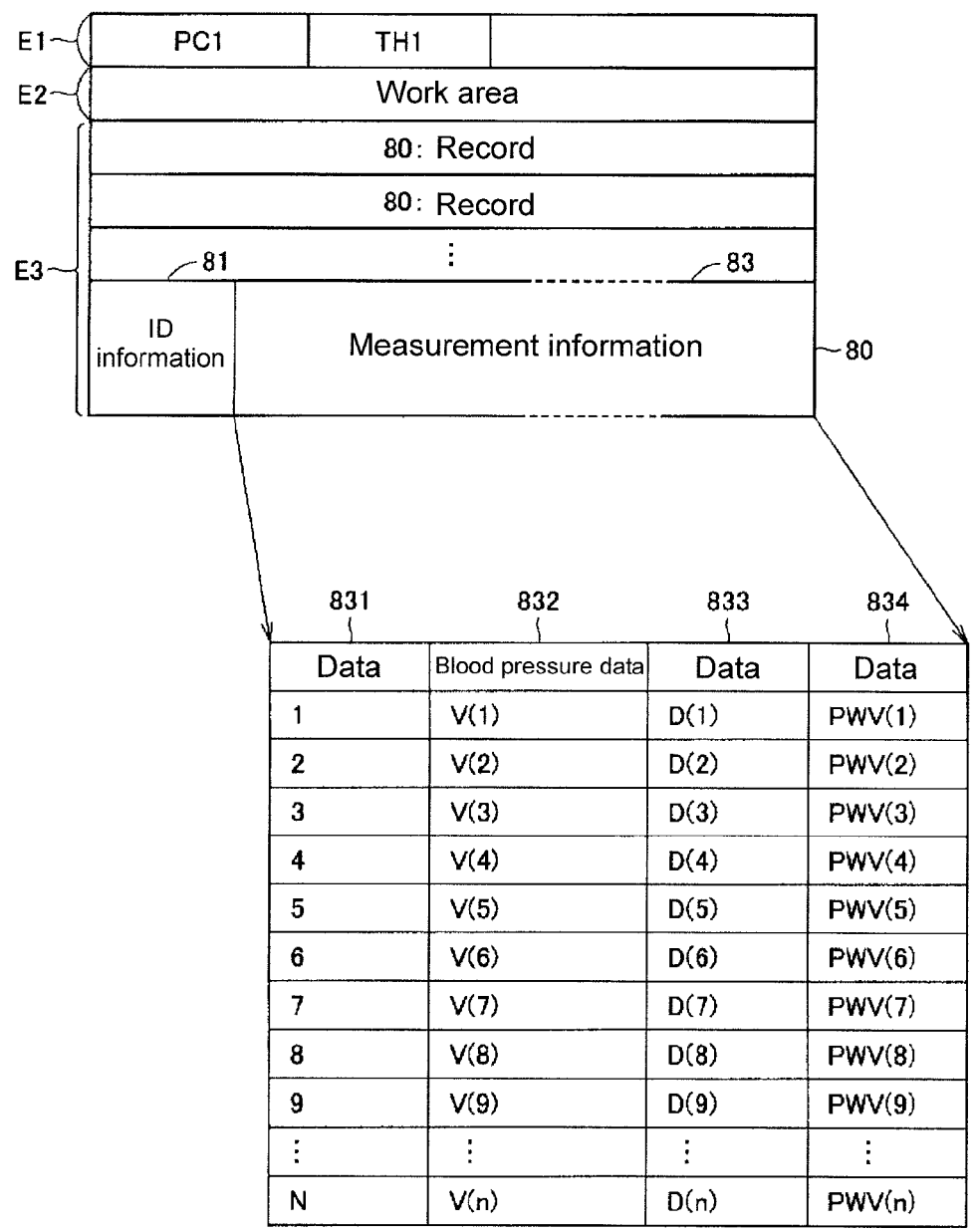
FIG. 5 is a diagram for explaining a storage example of measurement data according to the first embodiment of the present invention.

FIG. 5 is a diagram showing a data structure of the measurement data stored in the flash memory 43 in the first embodiment of the present invention.

Referring to FIG. 5, the flash memory 43 includes an area E1, a work area E2, and a storage area E3 of the measurement data. In the area E1, the cuff pressure data PC1 and the threshold TH1 are stored. Thresholds TH2 and TH3 described later are also stored in the area E1. The cuff pressure data PC1 is referred to for the detection of the control target value and the initial cuff pressure.

In the area E3, a plurality of pieces of measurement data 80 are stored. Each piece of the measurement data 80 includes a field 81 of "ID information" and a field 83 of measurement information as one example. In the field 81, the ID information inputted by the operation of the ID switch 41E at the time of blood pressure measurement is stored. In the field 83, data 831 measured by the timer 45 such as a measurement start date and time, a measurement period and the like of the measurement data, data 832 of the measured blood pressure, data 833 of the volume change elimination rate calculated by the volume change elimination rate calculating unit 110, and data 834 of the degree of arteriosclerosis (PWV) calculated by the arteriosclerosis degree calculating unit 111 are stored in association with one another.

Second Embodiment

In the present second embodiment, another processing procedure of the gain decision (step S26) by the gain decision unit 109 is described. The configuration and the other functions of the electronic sphygmomanometer 1 are similar to those in the first embodiment except that the procedure of the gain decision is different.

While in the foregoing first embodiment, as a condition for determining the convergence of the arterial volume change signal PGac, the amplitude reduction amount ΔPGac of the arterial volume change signal PGac is used, instead, a difference ΔΔPGac in the amplitude reduction amount of the arterial volume change signal PGac (a difference in the amplitude reduction amount ΔΔPGac=an amplitude reduction amount one pulse ahead ΔPGac−a current amplitude reduction amount ΔPGac) may be utilized. The processing procedure of the gain decision (step S26) according to the present second embodiment is described in accordance with a flowchart shown in FIG. 11.

Figure 11:
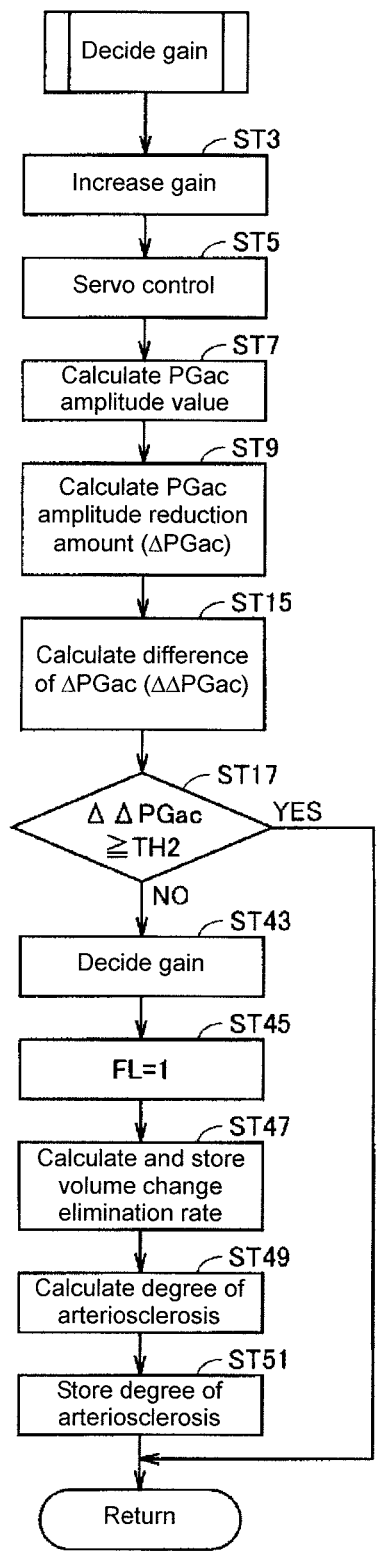
FIG. 11 is a flowchart of gain decision processing according to a second embodiment of the present invention.

Since in the processing of steps ST3 to ST9 of FIG. 11, the processing in steps ST3 to ST9 of FIG. 10 is executed, a description thereof is not repeated.

Subsequently, the gain decision unit 109 calculates the difference in the amplitude reduction amount ΔΔPGac is calculated, based on the amplitude reduction amount one pulse ahead ΔPGac−the current amplitude reduction amount ΔPGac (step ST15). The data of the amplitude reduction amount one pulse ahead ΔPGac is read from the internal memory of CPU 100.

Subsequently, when it is detected continuously in a plurality of pulses that the difference in the amplitude reduction amount ΔΔPGac becomes smaller than the predetermined threshold TH2 (NO in step ST17), the gain decision unit 109 determines that the amplitude of the arterial volume change signal PGac has converged to the minimum value.

Thereafter, the processing of steps ST43 to ST51 of FIG. 10 is similarly performed.

Here, the threshold TH2 is a value decided in advance by sampling from a number of subjects, and for example, a value of 10% of the maximum value of the amplitude of the arterial volume change signal PGac may be used.

Third Embodiment

In the present third embodiment, another processing procedure of the gain decision (step S26) by the gain decision unit 109 is described. The configuration and the other functions of the electronic sphygmomanometer 1 are similar to those in the first embodiment except that the procedure of the gain decision is different.

In place of the foregoing first and second embodiments, a processing procedure of the present embodiment may be used. In the present embodiment, since the property that the control error (the difference between the control target value and the current level of the arterial volume signal PGdc) becomes minimal in the servo gain is known, and by focusing attention on this property, a point when the control error in one pulse of the pulse wave becomes minimal is detected to thereby decide the optimal servo gain.

Figure 12:
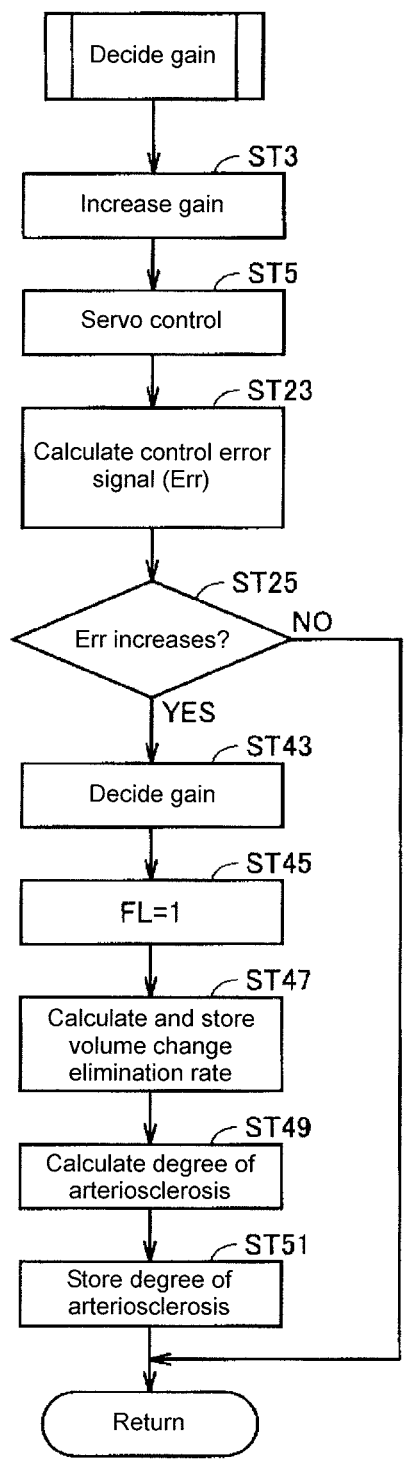
FIG. 12 is a flowchart of gain decision processing according to a third embodiment of the present invention.

The processing procedure of the gain decision (step S26) according to the present third embodiment is described in accordance with a flowchart shown in FIG. 12.

Since in the processing in steps ST3 to ST5 of FIG. 12, the processing in steps ST3 to ST5 of the FIG. 10 is executed, a description thereof is not repeated.

The gain decision unit 109, in step ST5, performs the servo control of the cuff pressure so that the difference between the level of the arterial volume signal PGdc and the control target value V0 is minimal. Subsequently, the gain decision unit 109 detects a control error signal Err in each pulse of the pulse wave detected in the process of this servo control (step ST23).

Here, the control error signal Err is calculated as a value obtained by squaring the difference between the control target value V0 and the level of the arterial volume signal PGdc, or as a value obtained by integrating an absolute value of the difference in one pulse of the pulse wave.

The gain decision unit 109 calculates the value of the control error signal Err in each pulse of the pulse wave, and the calculated value of the control error signal Err and the current value of the servo gain are stored in the internal memory of the CPU 100 in association with each other. Every time it is calculated in one pulse of the pulse wave, the value indicated by the control error signal Err calculated last is read from the memory, and the read value and a value indicated by the control error signal Err calculated this time are compared to detect whether or not the value of the control error signal Err has increased based on the comparison result. While it is not detected that the value has increased (NO in step ST25), the above-described operation is repeated.

Since the servo control unit 106 performs the PID control, the value of the control error signal Err should converge to a minimum value. Accordingly, when it is detected that the value of the control error signal Err has increased (YES in step ST25), the gain decision unit 109 decides the servo gain one pulse ahead, that is, the value of the servo gain one pulse ahead, which is read from the internal memory of the CPU 100, as the optimal value at the time point when the value of the control error signal Err converged (step ST43). Hereinafter, the processing in steps ST45 to ST51 of FIG. 10 is similarly performed.

Fourth Embodiment

The present fourth embodiment, another processing procedure of the gain decision (step S26) by the gain decision unit 109 is described. The configuration and the other functions of the electronic sphygmomanometer 1 are similar to those in the first embodiment except that the procedure of the gain decision is different. In place of the foregoing first to third embodiments, the gain decision procedure of the present fourth embodiment may be used.

Figure 13:
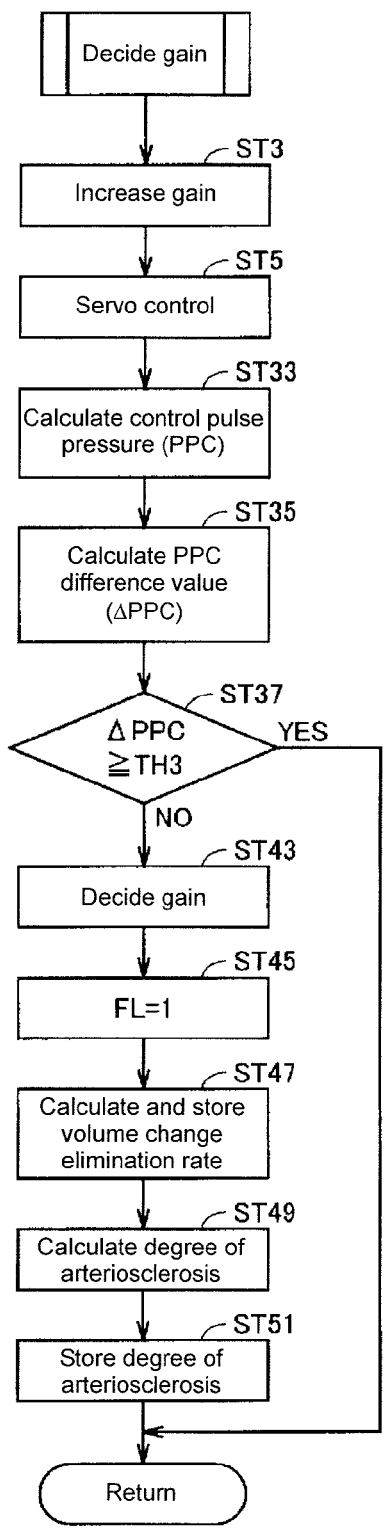
FIG. 13 is a flowchart of gain decision processing according to a fourth embodiment of the present invention.

In accordance with a flowchart shown in FIG. 13, a method of the gain decision processing according to the present fourth embodiment is described. Here, as the servo control unit 106 is increasing the servo gain at the constant rate, the magnitude of the pulsation (control pulse pressure) detected through the cuff pressure by the servo control of the servo control unit 106 largely increases at the beginning, but the increase amount gradually becomes smaller, and finally converges to a certain value. By focusing attention on this property, the gain decision unit 109 decides the optimal servo gain by detecting the convergence point of the control pulse pressure.

Referring to FIG. 13, firstly, the processing in steps ST3 and ST5 of FIG. 10 is similarly performed.

In the process in which the servo control is performed, the gain decision unit 109 detects a difference between the maximum value and the minimum value of the amplitude (referred to as a control pulse pressure PPC) in each pulse of the cuff pressure Pc, and stores the detected control pulse pressure PPC and the value of the servo gain at that time in association with each other in the internal memory of the CPU 100 (step ST33). A difference value ΔPPC indicating a difference from the control pulse pressure PPC one pulse ahead is calculated, based on the control pulse pressure PPC detected this time, and the control pulse pressure PPC detected one pulse ahead, which is read from the memory (step ST35).

If the gain decision unit 109 continuously detects that the calculated difference value ΔPPC becomes smaller than the threshold TH3 (NO in step ST37), it determines that the control pulse pressure PPC has converged, and decides the value at this time point as the servo gain for use in the blood pressure calculation processing (step ST43).

Hereinafter, the processing in steps ST45 to ST51 of FIG. 10 is similarly performed.

Here, the threshold TH3 is a value decided in advance by sampling from a number of subjects, and for example, 2.5 mmHg (a value of the error of 5% when the pulse pressure of the measured person is 50 mmHg) can be utilized.

According to the respective embodiments, the electronic sphygmomanometer 1 that measures the blood pressure according to the volume compensation method decides the optimal value of the servo gain at the time of the blood pressure measurement, using the arterial volume change signal PGac inherent to the individual. This allows the volume change elimination rate as a barometer of the degree of arteriosclerosis to be detected with a high accuracy.

In this manner, the above-described embodiments disclosed this time are illustrative in all points, and not limitative. The technical range of the present invention is defined by the scope of claims, and meanings equivalent to the description of the scope of claims and all modifications within the scope are included.

INDUSTRIAL APPLICABILITY

The present invention is effective in an apparatus that measures the blood pressure in accordance with the volume compensation method.

The invention claimed is:

1. An electronic sphygmomanometer to measure blood pressure in accordance with the volume compensation method, the electronic sphygmomanometer comprising:
   a cuff adapted for attaching to a measurement site of the blood pressure,
      wherein the measurement site is selected from the group consisting of: a site from a wrist to a base of an arm, and a site from an ankle to a base of a leg;
   a pressure detector to detect a cuff pressure representing a pressure inside the cuff;
   a volume detector provided in the cuff and intended to detect an arterial volume signal indicating a volume of an artery of the measurement site;
   a cuff pressure adjustment unit to adjust the cuff pressure by increasing and decreasing the pressure; and
   a control unit comprising:
      a servo control unit to servo-control the cuff pressure adjustment unit so that the volume of the artery becomes constant, based on the detected arterial volume signal after setting the cuff pressure to the initial cuff pressure;
      a volume change detector to detect an amount of change in the volume of the artery prior to constant volume, based on the detected arterial volume signal, while the control by the servo control unit is being performed,
   a first control unit comprising:
      a control target value detector to detect a control target value by controlling the cuff pressure adjustment unit until the cuff pressure becomes a specific pressure at which the volume change detector detects that the amount of volume change in the volume of the artery is maximum,
         wherein the control target value is a maximum value of the amount of change in the volume of the artery; and
      a cuff pressure setting unit to set the cuff pressure to an initial cuff pressure representing the specific pressure value;
   an amplitude ratio detector to detect a ratio between an amplitude of the arterial volume signal detected when the cuff pressure is set to the initial cuff pressure representing the specific cuff pressure, that is, when the volume change detector detects that the amount of change in the volume of the artery is maximum, and an amplitude of the arterial volume signal detected when the volume change detector detects that the amount of change in the volume of the artery is minimal; and
   an output unit to output the ratio of the amplitude detected by the amplitude ratio detector as a barometer of a degree of arteriosclerosis.

2. The electronic sphygmomanometer according to claim 1,
   wherein the servo control unit determines the arterial volume when the maximum amplitude of the arterial volume signal is detected to be a target value of the servo control, and
   based on a difference between the arterial volume indicated by the detected arterial volume signal and the target value, a servo gain is adjusted so that the amount of change in the volume of the artery detected by the volume change detector becomes minimal, by which the cuff pressure adjustment unit is servo-controlled by the servo control unit.

3. The electronic sphygmomanometer according to claim 2, wherein in a process of increasing the servo gain at a constant rate by the servo control unit, when the amount of change in the volume of the artery detected by the volume change detector converges, the amplitude ratio detector detects the ratio of the amplitude.

4. The electronic sphygmomanometer according to claim 1, further comprising a blood pressure measurement unit to continuously measure the blood pressure while the control by the servo control unit is being performed, wherein
   the blood pressure measurement unit has a decision unit to receive a detection signal from the pressure detector and decide a cuff pressure corresponding to the detection signal as the blood pressure, and
   when the volume change detector detects that the amount of change in the volume of the artery is minimal, the blood pressure decided by the decision unit is outputted by the blood pressure measurement unit.

5. The electronic sphygmomanometer according to claim 1, wherein in accordance with a correlationship between the ratio of the amplitude and the degree of arteriosclerosis, the control unit detects a degree of arteriosclerosis of the measurement site, based on the ratio of the amplitude detected by the amplitude ratio detector.

6. The electronic sphygmomanometer according to claim 3, wherein when it is detected that the amount of change in the volume of the artery detected by the volume change detector has a predetermined value or less, detected is that the amount of change in the volume of the artery is converged.

7. The electronic sphygmomanometer according to claim 3, wherein a difference between the amount of change in the volume of the artery in one pulse and the amount of change in the volume of the artery one pulse ahead is detected in each pulse of a pulse wave of the detected arterial volume signal, and when it is detected continuously in a plurality of pulses that the detected difference indicates a predetermined value or less, detected is that the amount of change in the volume of the artery is converged.

8. The electronic sphygmomanometer according to claim 3, wherein in the process of increasing the servo gain at the constant rate by the servo control unit, when a control error in one pulse of a pulse wave becomes minimal, detected is that the amount of change in volume of the artery has converged, and the control error indicates a difference between the arterial volume indicated by the detected arterial volume signal and the target value.

9. The electronic sphygmomanometer according to claim 3, wherein in the process of increasing the servo gain at the constant rate by the servo control unit, a magnitude of a pulsation detected from the cuff pressure by the servo control converges, so that the amount of change in the volume of the artery is converged.

* * * * *